US00RE45444E

(19) United States
(12) Reissued Patent
Miyata et al.

(10) Patent Number: US RE45,444 E
(45) Date of Reissued Patent: Mar. 31, 2015

(54) MEDICAL GUIDEWIRE

(71) Applicant: Asahi Intecc Co., Ltd., Nagoya-shi, Aichi-ken (JP)

(72) Inventors: Naohiko Miyata, Nagoya (JP); Satoshi Nagano, Nagoya (JP); Makoto Nishigishi, Nagoya (JP)

(73) Assignee: Asahi Intecc Co., Ltd., Nagoya-shi (JP)

(21) Appl. No.: 13/774,685

(22) Filed: Feb. 22, 2013

Related U.S. Patent Documents

Reissue of:
(64) Patent No.: 8,262,588
Issued: Sep. 11, 2012
Appl. No.: 12/797,973
Filed: Jun. 10, 2010

(30) Foreign Application Priority Data

Jun. 16, 2009 (JP) ..... 2009-143732

(51) Int. Cl.
*A61M 25/00* (2006.01)
*A61B 17/17* (2006.01)

(52) U.S. Cl.
CPC ..... *A61B 17/17* (2013.01)
USPC ..... 600/585

(58) Field of Classification Search
USPC ..... 600/433, 434, 585; 604/164.13
See application file for complete search history.

(56) References Cited

U.S. PATENT DOCUMENTS 4,748,986 A 6/1988 Morrison et al.
4,886,067 A * 12/1989 Palermo ..... 600/434
5,345,945 A * 9/1994 Hodgson et al. ..... 600/585
5,377,690 A 1/1995 Berthiaume
5,833,631 A 11/1998 Nguyen
6,620,114 B2 9/2003 Vrba et al.
6,805,676 B2 10/2004 Klint
7,713,215 B2 5/2010 Shriver
7,717,864 B1 5/2010 Grandfield et al.
7,883,474 B1 * 2/2011 Mirigian et al. ..... 600/585
2002/0183654 A1 12/2002 Zhou
2004/0082879 A1 * 4/2004 Klint ..... 600/585

(Continued)

FOREIGN PATENT DOCUMENTS

JP 08-173547 7/1996
JP 08-173547 A 7/1996

(Continued)

OTHER PUBLICATIONS

Aug. 19, 2013 Non-Final Rejection issued in co-pending U.S. Appl. No. 13/327,213.

(Continued)

*Primary Examiner* — Max Hindenburg
*Assistant Examiner* — Jonathan M Foreman
(74) *Attorney, Agent, or Firm* — Oliff PLC

(57) ABSTRACT

Provided is a guidewire including a core shaft, an outer flexible tube, and an inner flexible tube that surrounds a distal end portion of the core shaft. The inner flexible tube is disposed in the outer flexible tube so that a distal end thereof is positioned between the distal end of the core shaft and a proximal end of the core shaft so as to be separated from the core shaft. A first joint is formed so as to join the distal end of the inner flexible tube to the core shaft. At least one second joint is formed so as to join the outer flexible tube to the inner flexible tube. The at least one second joint is positioned between the first joint and the proximal end of the core shaft.

13 Claims, 8 Drawing Sheets

(56) References Cited

U.S. PATENT DOCUMENTS

| | | | | |
|---|---|---|---|---|
| 2004/0122340 | A1 | 6/2004 | Vrba et al. | |
| 2004/0210163 | A1* | 10/2004 | Osawa et al. | 600/585 |
| 2005/0054951 | A1* | 3/2005 | Parins | 600/585 |
| 2006/0235337 | A1* | 10/2006 | Vrba et al. | 600/585 |
| 2008/0194992 | A1 | 8/2008 | Satou et al. | |
| 2009/0005706 | A1 | 1/2009 | Miyata et al. | |
| 2009/0036832 | A1 | 2/2009 | Skujins et al. | |
| 2009/0112126 | A1 | 4/2009 | Keating et al. | |
| 2009/0112127 | A1 | 4/2009 | Keating et al. | |
| 2010/0168619 | A1* | 7/2010 | Elsesser | 600/585 |

FOREIGN PATENT DOCUMENTS

| | | | |
|---|---|---|---|
| JP | 09-182800 | | 7/1997 |
| JP | 09-182800 | A | 7/1997 |
| JP | A-2004-313570 | | 11/2004 |
| JP | A-2005-528126 | | 9/2005 |
| JP | 2005-270466 | A | 10/2005 |
| JP | A-2005-270466 | | 10/2005 |
| JP | 2006-511304 | A | 4/2006 |
| JP | A-2006-511304 | | 4/2006 |
| JP | 2008-161491 | A | 7/2008 |
| JP | A-2008-161491 | | 7/2008 |
| JP | 2008-194185 | | 8/2008 |
| JP | 2008-194185 | A | 8/2008 |
| JP | 2009-00337 | A | 1/2009 |
| JP | A-2009-00337 | | 1/2009 |
| WO | 98/18516 | A1 | 5/1998 |
| WO | WO 98/18516 | A1 | 5/1998 |
| WO | WO 03/030982 | A2 | 4/2003 |
| WO | WO 2004/060462 | A2 | 7/2004 |

OTHER PUBLICATIONS

May 3, 2013 Office Action issued in U.S. Appl. No. 13/327,213.
Jan. 14, 2013 Office Action issued in U.S. Appl. No. 13/327,213.
Jun. 26, 2012 Office Action issued in Chinese Patent Application No. 201010206562.3 (with translation).
May 6, 2011 Office Action issued in Japanese Patent Application No. 2009-143732 (with translation).
Oct. 18, 2010 Extended European Search Report issued in European Patent Application No. 10165916.7.
Oct. 16, 2012 Office Action issued in Chinese Patent Application No. 201110424178.5 (with translation).
Dec. 7, 2011 Office Action issued in Japanese Patent Application No. 2009-143732 (with translation).
Mar. 8, 2012 Extended European Search Report issued in European Application No. 11195908.6.
Nov. 25, 2013 Office Action issued in U.S. Appl. No. 13/327,213.
Office Action issued in U.S. Appl. No. 13/327,213 dated Apr. 11, 2014.
Dec. 5, 2014 Office Action issued in European Patent Application No. 10165916.7.
Dec. 5, 2014 Office Action issued in European Patent Application No. 11195908.6.
Extended European Search Report dated Oct. 18, 2010 for corresponding European Application No. 10165916.7.
JP Office Action with English summary and English translation for JP Application No. 2009-143732 mailed on May 6, 2011.
English Translation of Japanese Office Action for corresponding JP Application No. 2009-143732 mailed on Dec. 7, 2011.

* cited by examiner

MEDICAL GUIDEWIRE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

1. Field of the Invention

The present invention relates to a medical guidewire used for medical purposes such as inserting a catheter into a blood vessel, a ureter, or an organ or inserting an indwelling device into part of a blood vessel suffering from an aneurysm.

2. Description of the Related Art

In general, it is required that a medical guidewire have a flexible distal end portion, and it is also required that the medical guidewire smoothly transmit an operation performed at the proximal end portion to the distal end portion. In order to fulfill such requirements, a guidewire 100 of the related art includes a core shaft 101 and a coil spring 102 that surrounds the core shaft 101, and the diameter of a distal end portion 103 of the core shaft 101 is made small so as to improve flexibility (see FIG. 8).

When using the guidewire 100 to guide a device, such as a catheter or an indwelling device, to a target region in a human body, the distal end portion of the guidewire 100 may be unintentionally bent into a U-shape. For some operations, the guidewire 100 is bent into a U-shape before insertion in order to prevent misinsertion of the guidewire 100 into a nontarget blood vessel or in order that the guidewire 100 is securely held by a blood vessel wall by using the resilience of the guidewire 100.

When performing such operations, in which the guidewire 100 is intentionally bent into a U-shape before insertion into a blood vessel, there are cases in which only a part of the distal end portion of the guidewire 100 is bent into a U-shape and there are cases in which the entirety of the distal end portion of the guidewire 100 is bent into a U-shape. Which case occurs depends on the diameter or the shape of a target blood vessel into which the guidewire 100 is inserted.

The guidewire 100 of the related art has a low rigidity because the diameter of the distal end portion 103 of the core shaft 101 is small, so that the guidewire 100 is easily bent due to stress concentration. Once the core shaft 101 is bent into a U-shape, plastic deformation occurs, so that the core shaft 101 has a residual angle even after the U-shaped bending is released. Due to the presence of the residual angle, the operability of the guidewire 100 is reduced and the guidewire 100 may have to be replaced during the operation.

A modification of the guidewire 100 uses a stranded wire as the distal end portion 103 of the core shaft 101 (see Japanese Unexamined Patent Application Publication No. 2008-161491). The guidewire 100 has a certain degree of resilience after having been bent. However, when the guidewire 100 is bent into a U-shape having a large curvature, the guidewire 100 may not recover its original shape even after the U-shaped bending is released. Therefore, the drawback due to the presence of a residual angle remains.

Another modification of the guidewire 100 includes a radiopaque inner coil disposed between the coil spring 102 and the core shaft 101 (see Japanese Unexamined Patent Application Publication No. 08-173547 and Japanese Unexamined Patent Application Publication (Translation of PCT Application) No. 2006-511304). With the guidewire 100, the rigidity of a part of the distal end portion having the inner coil is increased. However, this modification also has the drawback due to the presence of a residual angle after having been bent into a U-shape.

SUMMARY OF THE INVENTION

The object of the present invention, which has been achieved in order to overcome the drawback described above, is to improve the resilience of a distal end portion of a guidewire after the distal end portion has been bent into a U-shape and to prevent the U-shaped bend from becoming larger during use.

According to an aspect of the present invention, there is provided a medical guidewire (hereinafter referred to as a "guidewire") including a core shaft including a distal end portion having a small diameter; an outer flexible tube that surrounds an outer surface of the core shaft; and an inner flexible tube disposed in the outer flexible tube, the inner flexible tube surrounding the distal end portion of the core shaft. With this structure, the resilience of the guidewire is improved because the inner flexible tube surrounds the outer surface of the core shaft.

A distal end of the core shaft is joined to a distal end of the outer flexible tube. The inner flexible tube is disposed so that a distal end thereof is positioned between the distal end of the core shaft and a proximal end of the core shaft so as to be separated from the distal end of the core shaft. A first joint is formed so as to join the distal end of the inner flexible tube to the core shaft, and at least one second joint is formed so as to join the outer flexible tube to the inner flexible tube, the at least one second joint being positioned between the first joint and the proximal end of the core shaft.

With this structure, the rigidity of a portion of the guidewire between the first joint and the distal end of the guidewire and the rigidity of a portion of the guidewire between the first joint and the proximal end of the guidewire differ from each other. Moreover, the guidewire has a high rigidity at the first joint. That is, the portion of the guidewire between the first joint and the distal end is constituted by "the outer flexible tube and the core shaft" and the portion of the guidewire between the first joint and the proximal end is constituted by "the outer flexible tube, the inner flexible tube, and the core shaft". Therefore, these portions of the guidewire, which are divided by the first joint, have different rigidities. Moreover, the guidewire has a high rigidity at the first joint, because the distal end of the inner flexible tube and the core shaft are fixed to each other at the first joint. The guidewire has a high rigidity at the second joint because the outer flexible tube and the inner flexible tube are fixed to each other at the second joint.

Therefore, even when the distal end portion of the guidewire is bent into a U-shape when the guidewire is inserted into the lumen of a blood vessel or the like, the portion of the guidewire between the first joint and the proximal end is not bent due to the presence of the first joint having a high rigidity. As a result, only the distal end portion of the guidewire, which has a high flexibility, is bent into a U-shape. That is, only the distal end portion having a high resilience is bent into a U-shape, so that the guidewire is not plastically deformed in the bent state. Therefore, the resilience of the guidewire can be improved.

Even if the first joint fails to stop the U-shaped bending of the guidewire and the portion of the guidewire between the first joint and the proximal end is bent, a portion between the second joint and the proximal end is not easily bent due to the presence of the second joint having a high rigidity, which is formed at a position between the first joint and the proximal end of the guidewire. That is, the first joint and the second joint prevent the U-shaped bend of the guidewire from becoming larger in a stepwise manner. Because the second joint stops the U-shaped bending, only a portion of the guidewire in which the inner flexible tube is disposed and which has a high resilience is bent into a U-shape. Therefore, the guidewire has a high resilience after the bending is released.

When performing operations in which the guidewire is intentionally bent into a U-shape before insertion into a blood vessel, there are cases in which only a part of the distal end portion of the guidewire is bent into a U-shape and there are cases in which the entirety of the distal end portion of the guidewire is bent into a U-shape. Which case occurs depends on the diameter or the shape of a target blood vessel into which the guidewire is inserted. With the guidewire according to the aspect of the invention, a user can easily operate the guidewire in accordance with the type of an operation by selectively using the functions of the first joint and the second joint.

DESCRIPTION OF THE PREFERRED EMBODIMENTS

A guidewire according to a first embodiment includes a core shaft, an outer flexible tube, and an inner flexible tube. The core shaft has a distal end portion having a small diameter. The outer flexible tube surrounds the outer surface of the core shaft. The inner flexible tube is disposed in the outer flexible tube and surrounds the distal end portion of the core shaft. A distal end of the core shaft is joined to a distal end of the outer flexible tube. A distal end of the inner flexible tube is positioned between the distal end of the core shaft and a proximal end of the core shaft so as to be separated from the distal end of the core shaft. A first joint is formed so as to join the distal end of the inner flexible tube to the core shaft. At least one second joint is formed so as to join the outer flexible tube to the inner flexible tube. The at least one second joint is positioned between the first joint and the proximal end of the core shaft.

The distal end portion of the core shaft includes a step portion and a small-diameter portion that extends from the step portion to the distal end of the core shaft. The second joint is formed near to the step portion in the axial direction. The inner flexible tube is a hollow stranded-wire coil made by stranding multiple metal strands. The inner flexible tube has a tapered shape in which the outside diameter gradually decreases toward the distal end. The inside diameter of the inner flexible tube is uniform from the distal end to the proximal end. The metal strands of the hollow stranded-wire coil are made of a stainless steel alloy.

The outer flexible tube is a single-wire coil including a large-pitch portion that extends from the distal end of the outer flexible tube toward the proximal end by a certain distance. The large-pitch portion has a pitch larger than that of a proximal end portion of the outer flexible tube. A proximal end of the large-pitch portion is positioned between the first joint and the proximal end of the outer flexible tube.

A guidewire according to a second embodiment includes a stranded wire that is disposed in the inner flexible tube. The stranded wire extends parallel to the distal end portion of the core shaft.

EMBODIMENTS

Structure of First Embodiment

Figure 1:
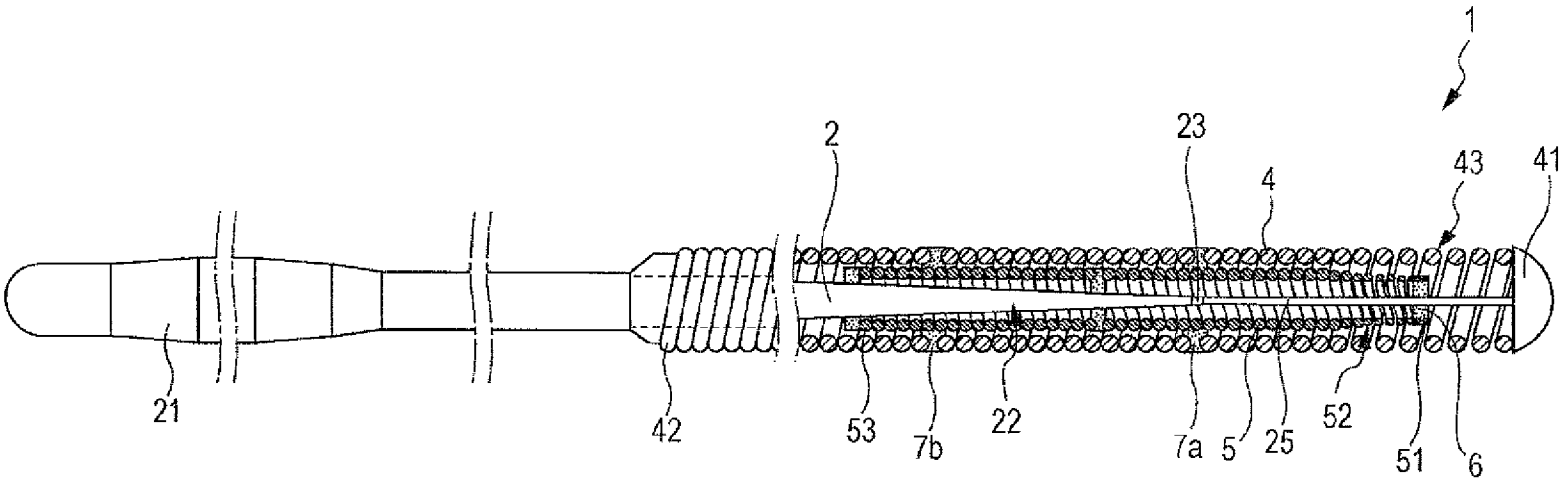
FIG. 1 is a partially sectional side view of a guidewire according to a first embodiment.
Figure 2:
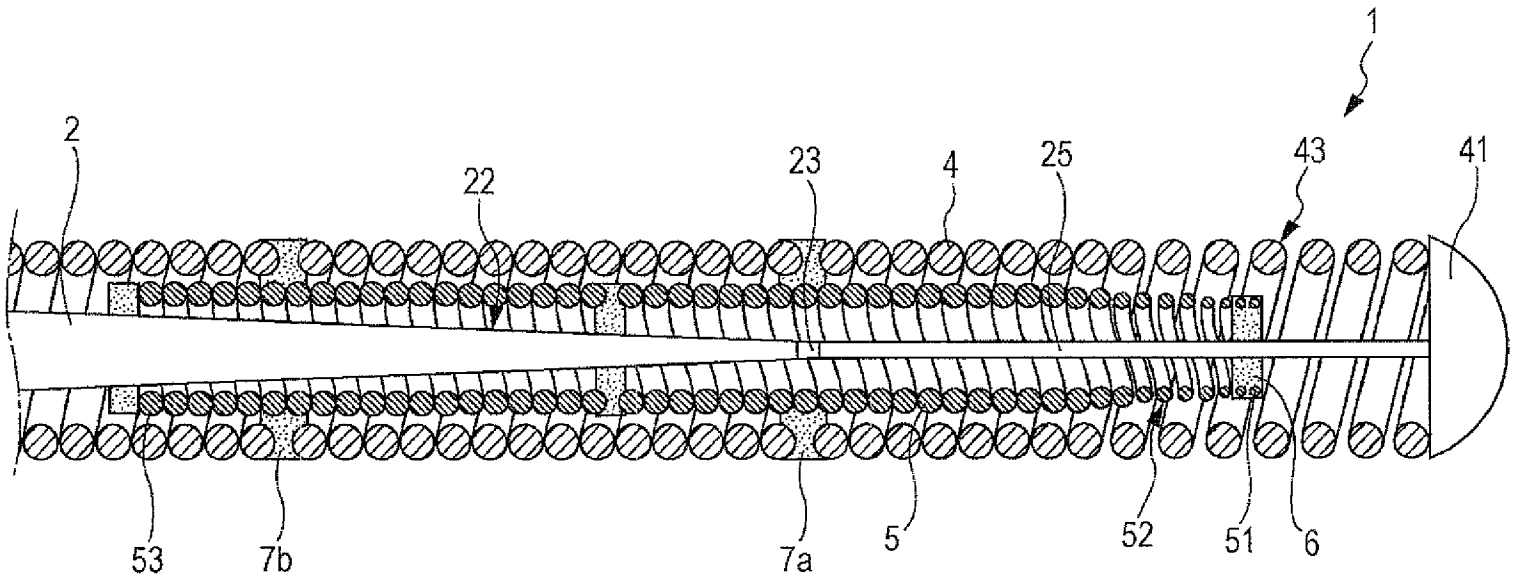
FIG. 2 is a sectional side view of a distal end portion of the guidewire according to the first embodiment.
Figure 3A:
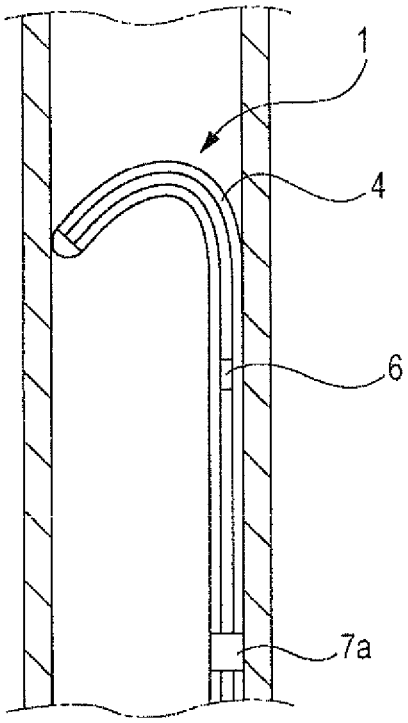
FIGS. 3A and 3B illustrate the distal end portion of the guidewire according to the first embodiment that is being bent into a U-shape in a blood vessel.
Figure 3B:
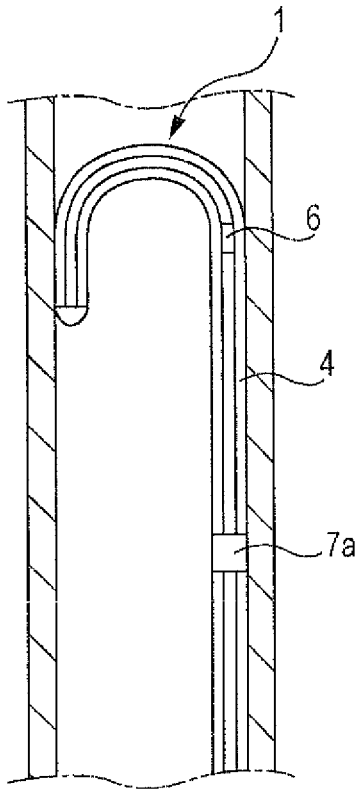

Referring to FIGS. 1 to 3, the structure of a guidewire 1 according to the first embodiment will be described. In FIGS. 1 and 2, the right side is the distal end side, and the left side is the proximal end side. The guidewire 1 includes a core shaft 2, an outer flexible tube 4 through which the core shaft 2 is inserted, and an inner flexible tube 5 disposed in the outer flexible tube 4. The core shaft 2 is inserted through the inner flexible tube 5, and the inner flexible tube 5 is inserted through the outer flexible tube 4.

The core shaft 2 is made of a stainless steel alloy. The core shaft 2 has a grip 21, which has a large diameter, positioned adjacent to the proximal end thereof and a distal end portion 22, which has a small diameter, positioned adjacent to the distal end thereof. The diameter of the distal end portion 22 of the core shaft 2 decreases stepwise. The distal end portion 22 of the core shaft includes a step portion 23 and a small-diameter portion 25 that extends from the step portion 23 to the distal end of the core shaft 2. In the first embodiment, the small-diameter portion 25 has an outside diameter of, for example, 0.03 mm.

The outer flexible tube 4 is a single-wire coil made of a stainless steel strand. In the first embodiment, for example, the stainless steel strand has an outside diameter of 0.05 mm and the outer flexible tube 4 has an outside diameter of 0.355 mm. In order to provide flexibility to the distal end portion of the outer flexible tube 4, the outer flexible tube 4 includes a large-pitch portion 43, which has a larger coil pitch, in the distal end portion thereof. The large-pitch portion 43 extends in the axial direction from the distal end of the outer flexible tube 4 to a position between a distal end 51 of the inner flexible tube 5 (described below) and the proximal end of the outer flexible tube 4. As long as the outer flexible tube 4 has flexibility, the outer flexible tube 4 need not be a single-wire coil and may instead be a hollow stranded-wire coil, a resin tube, or the like.

The outer flexible tube 4 surrounds only a distal end portion of the core shaft 2. A proximal end 42 of the outer flexible tube 4 is fixed to an outer surface of a large-diameter portion of the core shaft 2 near to the proximal end. An outer surface of the outer flexible tube 4 is coated with a hydrophilic resin.

The inner flexible tube 5 is a hollow stranded-wire coil made of multiple stainless steel strands. The hollow stranded-wire coil may be made by stranding multiple strands around a core by using a wire stranding machine and then removing the core, or by stranding multiple strands into a hollow shape. In the first embodiment, for example, the inner flexible tube 5, which has an outside diameter of 0.188 mm, is formed by stranding six stainless steel strands each having an outside diameter of 0.04 mm, so that the flexibility and the torque transmission are well balanced. A distal end portion 52 of the inner flexible tube 5 is electro-polished so that the outside diameter decreases toward the distal end. The inside diameter of the inner flexible tube 5 is uniform from the proximal end to the distal end.

The inner flexible tube 5 has an outside diameter that is smaller than the inside diameter of the outer flexible tube 4. The inner flexible tube 5 has a length in the axial direction that is smaller than that of the outer flexible tribe 4. The distal end 51 of the inner flexible tube 5 is positioned between the distal end of the outer flexible tube 4 and the proximal end 42 of the outer flexible tube 4 in the axial direction. A proximal end 53 of the inner flexible tube 5 is positioned between the proximal end 42 of the outer flexible tube 4 and the distal end of the outer flexible tube 4 in the axial direction.

The distal end 51 of the inner flexible tube 5 is positioned between the distal end of the core shaft 2 and a proximal end of the small-diameter portion 25. The proximal end 53 of the inner flexible tube 5 is positioned between the step portion 23 and the proximal end of the core shaft 2. That is, the inner flexible tube 5 is disposed so that the distal end 51 of the inner flexible tube 5 is positioned between the distal end of the core shall 2 and the proximal end of the core shaft 2 so as to be separated from the core shaft 2 in the axial direction.

In the guidewire 1, a first joint 6 is formed so as to join the distal end 51 of the inner flexible tube 5 to the core shaft 2. To be specific, the first joint 6 is formed by soldering the distal end of the inner flexible tube 5 to the core shaft 2. A proximal end of the large-pitch portion 43 is positioned between the first joint 6 and the proximal end of the outer flexible tube 4. The proximal end 53 of the inner flexible tube 5 is fixed to the outer surface of the core shaft 2.

In the guidewire 1, two second joints 7a and 7b are formed so as to join the outer flexible tube 4 to the inner flexible tube 5 at positions between the first joint 6 and the proximal end of the outer flexible tube 4. The second joint 7a is formed by soldering the outer flexible tube 4 to the inner flexible tube 5 at a position corresponding to the step portion 23 in the axial direction. The second joint 7b is formed by soldering the outer flexible tube 4 to the inner flexible tube 5 at a position between the second joint 7a and the proximal end 53 of the inner flexible tube 5 in the axial direction.

Operational Effect of the First Embodiment

In the guidewire 1, the diameter of the distal end portion 22 of the core shaft 2 decreases stepwise toward the distal end. The inner flexible tube 5 is disposed in the outer flexible tube 4 and surrounds the distal end portion 22 of the core shaft 2. With this structure, the inner flexible tube 5 surrounds the distal end portion 22 of the core shaft 2, which has a small diameter in order to increase flexibility. Therefore, the resilience of the guidewire 1 is improved.

The inner flexible tube 5 is disposed so that the distal end 51 thereof is positioned between the distal end of the core shaft 2 and the proximal end of the core shaft 2 so as to be separated from the distal end of the core shaft 2. The first joint 6 is formed so as to join the distal end 51 of the inner flexible tube 5 to the core shaft 2.

With this structure, the rigidity of a portion of the guidewire 1 between the first joint 6 and the distal end of the guidewire 1 and the rigidity of a portion of the guidewire 1 between the first joint 6 and the proximal end of the guidewire 1 differ from each other. Moreover, the guidewire 1 has a high rigidity at the first joint 6. That is, the portion of the guidewire 1 between the first joint 6 and the distal end is constituted by "the outer flexible tube 4 and the core shaft 2" and the portion of the guidewire 1 between the first joint 6 and the proximal end is constituted by "the outer flexible tube 4, the inner flexible tube 5, and the core shaft 2". Therefore, these portions of the guidewire 1, which are divided by the first joint 6, have different rigidities. Moreover, the guidewire 1 has a high rigidity at the first joint 6, because the first joint 6 is formed by soldering the distal end 51 of the inner flexible tube 5 to the core shaft 2.

Therefore, even when the guidewire 1 is bent into a U-shape when the guidewire 1 is inserted into the lumen of a blood vessel or the like, the portion of the guidewire 1 between the first joint 6 and the proximal end is not bent due to the presence of the first joint 6 having a high rigidity. That is, even when the guidewire 1 is unintentionally bent in a blood vessel (see FIG. 3A) and a user inserts the guidewire 1 deeper into the blood vessel, the bending stops in front of the first joint 6 because the first joint 6 has a high rigidity (see FIG. 3B). Therefore, the U-shaped bend does not become larger.

As a result, only the distal end portion of the guidewire 1, which has a high flexibility, is bent into a U-shape. That is, only the distal end portion having a high resilience is bent into a U-shape, so that the guidewire 1 is not plastically deformed in the bent state. Therefore, the resilience of the guidewire 1 is improved.

Figure 4:
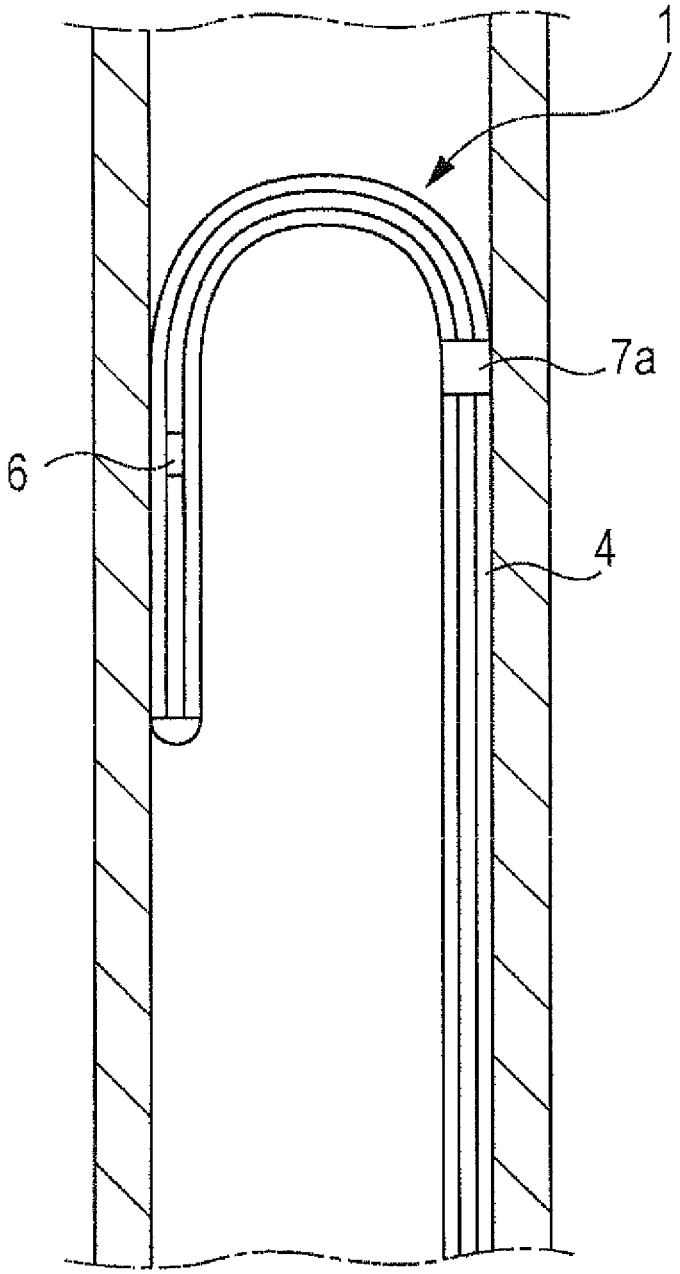
FIG. 4 illustrates the distal end portion of the guidewire according to the first embodiment that is being bent into a U-shape in a blood vessel.

In the guidewire 1, two second joints 7a and 7b are formed so as to join the outer flexible tube 4 to the inner flexible tube 5 at positions between the first joint 6 and the proximal end of the core shaft 2. With this structure, even if the first joint 6 fails to stop the U-shaped bending of the guidewire 1, and the portion of the guidewire 1 between the first joint 6 and the proximal end is bent, a portion between the second joints 7a and 7b and the proximal end is not easily bent due to the presence of the second joints 7a and 7b having high rigidities, which are formed at positions between the first joint 6 and the proximal end of the core shaft 2 (see FIG. 4). That is, the first joint 6 and the second joints 7a and 7b prevent the U-shaped bend of the guidewire 1 from becoming larger in a stepwise manner. Because the second joints 7a and 7b stop the U-shaped bending, only a portion of the guidewire 1 in which the inner flexible tube 5 is disposed and which has a high resilience is bent into a U-shape. Therefore, the guidewire 1 has a high resilience after the bending is released.

When performing operations in which the guidewire 1 is intentionally bent into a U-shape before insertion into a blood vessel, there are cases in which only a part of the distal end portion of the guidewire 1 is bent into a U-shape and there are cases in which the entirety of the distal end portion of the guidewire 1 is bent into a U-shape. Which case occurs depends on the diameter or the shape of a target blood vessel into which the guidewire 1 is inserted. The first joint 6 and the second joints 7a and 7b prevent excessive U-shaped bending of the guidewire 1 in a stepwise manner. Therefore, a user can easily operate the guidewire 1 by selectively using the functions of the first joint 6 and the second joints 7a and 7b in accordance with the type of the operation.

That is, when inserting the guidewire 1 into a small blood vessel, the guidewire 1 is bent at a position between the first joint 6 and the distal end. In this case, the first joint 6 serves to prevent the U-shaped bend from becoming larger. When the guidewire 1 is bent into a U-shape and then inserted into a large blood vessel, a portion of the guidewire 1 is bent at a position between the first joint 6 and the proximal end and then inserted into the blood vessel. In this case, the second joints 7a and 7b serve to prevent the U-shaped bend from becoming larger (see FIG. 4). In either case, the U-shaped bend is limited to a portion having a high resilience, so that the guidewire 1 easily returns to its original shape when the bending is released.

In the first embodiment, there is a difference in the rigidities of portions of the core shaft 2 sandwiching the step portion 23, and the second joint 7a is formed at a position near to the step portion 23. Therefore, there exists a substantial difference in rigidity between the portions of the guidewire 1 sandwiching the second joint 7a. Therefore, the second joint 7a more effectively prevents the U-shaped bend from becoming larger.

The outer flexible tube 4 is a single-wire coil including the large-pitch portion 43, which extends from the distal end of the outer flexible tube 4 toward the proximal end by a certain distance. The large-pitch portion 43 has a pitch larger than that of the proximal end portion of the outer flexible tube 4. The proximal end of the large-pitch portion 43 is positioned between the first joint 6 and a proximal end of the outer flexible tube 4. With this structure, the distal end of the guidewire 1 has flexibility, and the guidewire 1 has a smoother gradation in rigidity.

That is, the guidewire 1 according to the first embodiment has a structure having a gradation in rigidity in which the flexural rigidity gradually increases from the distal end toward the proximal end. To be specific, in the guidewire 1, a portion constituted by "the large-pitch portion 43 of the outer flexible tube 4 and the core shaft 2", a portion constituted by "the large-pitch portion 43 of the outer flexible tube 4, the inner flexible tube 5, and the core shaft 2", and a portion constituted by "a normal-pitch portion of the outer flexible tube 4, the inner flexible tube 5, and the core shaft 2" are arranged in this order from the distal end of the guidewire 1. The flexural rigidity gradually increases in this order. The remaining portion of the guidewire 1 near to the proximal end has a higher flexural rigidity, because the core shaft 2 has a larger diameter. Therefore, occurrence of stress concentration due to a sharp difference in rigidity is suppressed, so that the torque transmission is improved.

Because a hollow stranded-wire coil is used as the inner flexible tube 5, the torque transmission is improved as compared with a case in which a single-wire coil is used as the inner flexible tube 5. Therefore, a user can operate the guidewire 1 at will, so that the treatment time can be reduced. The distal end portion 52 of the inner flexible tube 5 has a tapered shape in which the diameter gradually decreases toward the distal end. Therefore, the gradation in the rigidity of the guidewire 1 can be made more moderate and smoother. The distal end portion of the inner flexible tube 5 has a small diameter, so that the flexibility of the guidewire 1 is improved and the guidewire 1 can be more easily inserted into a peripheral lumen.

The inside diameter of the inner flexible tube 5 is uniform from the distal end to the proximal end. Therefore, the core shaft 2 can be easily inserted into the inner flexible tube 5, so that the guidewire 1 can be easily assembled.

The metal strands of the hollow stranded-wire coil are made of a stainless steel alloy. Therefore, the rigidity of the inner flexible tube 5 is increased, so that the torque transmission and the operability of the guidewire 1 are improved.

Structure of Second Embodiment

Figure 5:
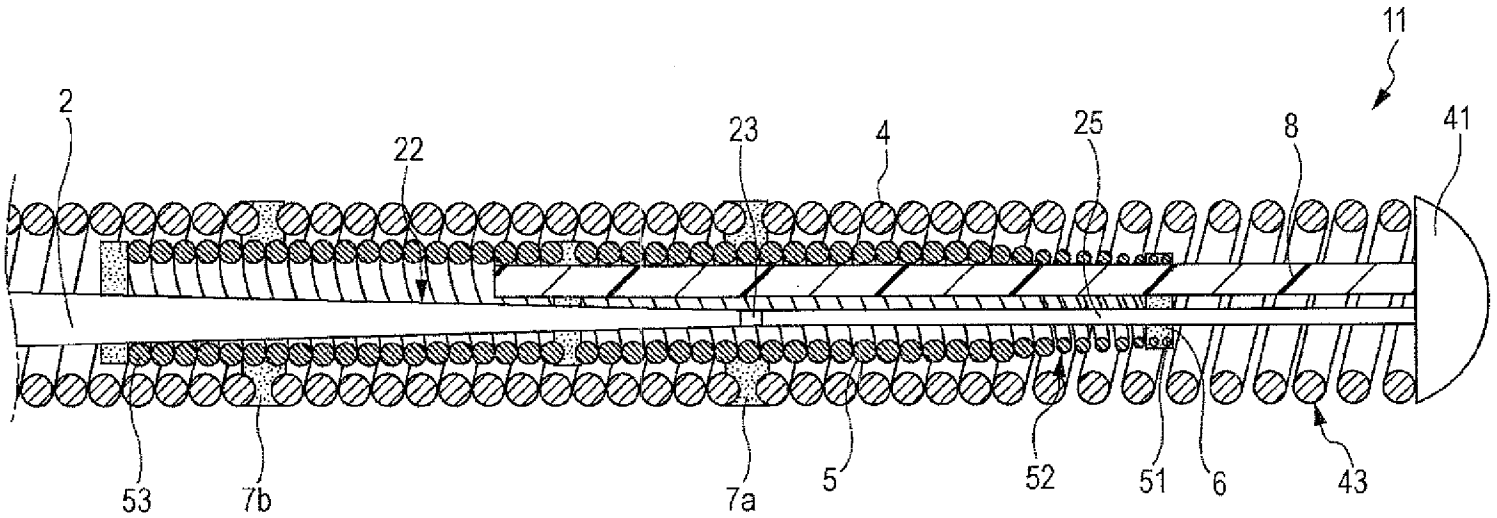
FIG. 5 is a sectional side view of a distal end portion of a guidewire according to a second embodiment.

Referring to FIG. 5, the structure of a guidewire 11 according to a second embodiment will be described with an emphasis on the differences from the first embodiment. In FIG. 5, the right side is the distal end side, and the left side is the proximal end side. The guidewire 11 includes a stranded wire 8 disposed in the inner flexible tube 5. The stranded wire 8 extends parallel to the distal end portion 22 of the core shaft 2. In the guidewire 11, the core shaft 2 and the stranded wire 8 are inserted through the inner flexible tube 5, and the inner flexible tube 5 is inserted through the outer flexible tube 4.

The stranded wire 8 is made by stranding metal strands made of, for example, a stainless steel alloy. In the second embodiment, for example, the stranded wire 8 is made by stranding seven stainless steel strands each having an outside diameter of 0.014 mm. The stranded wire 8 is disposed parallel to the distal end portion 22 of the core shaft 2. A distal end of the stranded wire 8 and the distal end of the core shaft 2 are soldered to a brazed end portion 41 disposed at the distal end of the outer flexible tube 4. A proximal end of the stranded wire 8 is positioned between the proximal end of the small-diameter portion 25 and the proximal end of the core shaft 2. The proximal end of the stranded wire 8 and the core shaft 2 are soldered to the inner flexible tube 5.

Operational Effect of the Second Embodiment

The strands of the stranded wire 8 can move slightly relative to each other. Therefore, the stranded wire 8 has a high degree of freedom, a high flexibility, a high resistance to plastic deformation, and a high resilience. Therefore, by disposing the stranded wire 8, which has resistance to plastic deformation, parallel to the distal end portion 22 of the core shaft 2, which has a small diameter and thus has flexibility, the resilience of the guidewire 11 after being bent into a U-shape is improved.

Modification

In the first and second embodiments, the diameter of the distal end portion 22 of the core shaft 2 decreases stepwise toward the distal end. Alternatively, the distal end portion 22 may be tapered toward the distal end.

In the first and second embodiments, the core shaft 2 is made of a stainless steel alloy. Alternatively, a part of the core shaft 2 near to the distal end (at least the small-diameter portion 25) may be made of a pseudoelastic alloy having a high resilience (for example, Ni—Ti alloy), and a part of the core shaft 2 near to the proximal end may be made of a stainless steel alloy. With this structure, the resilience of the distal end portion of the guidewire 1 or 11 is improved, and the torque transmission and the operability of the guidewire 1 or 11 are improved.

Figure 6:
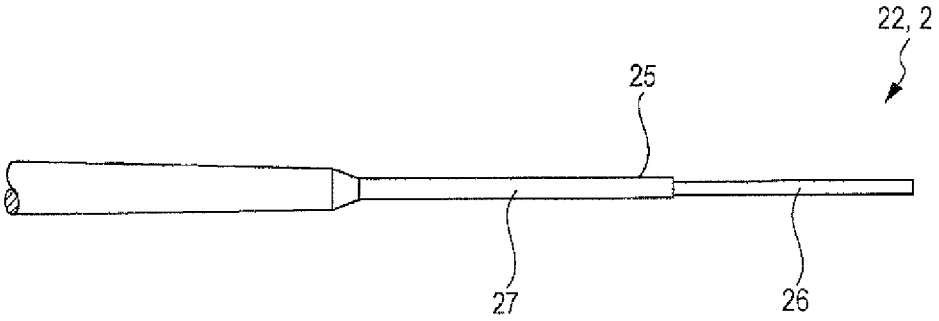
FIG. 6 is a partial side view of a core shaft of a guidewire according to a modification.

As illustrated in FIG. 6, a part of the small-diameter portion 25 near to the distal end may be made of a stainless steel alloy (a first distal end portion 26), a part of the small-diameter portion 25 near to the proximal end may be made of a pseudoelastic alloy (a second distal end portion 27), and a part of the core shaft 2 between the small-diameter portion 25 and the proximal end of the core shaft 2 may be made of a stainless steel alloy. With this structure, the pseudoelastic alloy improves the resilience of the distal end portion 22 of the core shaft 2. Moreover, because the portions made of a stainless steel alloy are provided to both sides of the part made of a pseudoelastic alloy, a torque applied to the proximal end portion of the guidewire 1 or 11 can be reliably transmitted to the distal end portion, so that the torque transmission and the operability of the guidewire 1 or 11 can be further improved.

In the first and second embodiments, the distal end portion 52 of the inner flexible tube 5 is tapered toward the distal end. Alternatively, the diameter of the distal end portion 52 may decrease stepwise toward the distal end.

In the first and second embodiments, the inner flexible tube 5 is made of only stainless steel strands. Alternatively, the inner flexible tube 5 may be made of only pseudoelastic alloy strands. With this structure, the resilience of the inner flexible tube 5 can be further increased. As a further alternative, the inner flexible tube 5 may be formed by combining stainless steel strands and pseudoelastic alloy strands (for example, three stainless steel strands and three pseudoelastic alloy strands). In this case, the stainless steel alloy increases the rigidity of the inner flexible tube 5, while the pseudoelastic alloy increases the resilience of the inner flexible tube 5. Therefore, the torque transmission, the operability, and the resilience of the guidewire 1 or 11 are improved.

In the first and second embodiments, the outer flexible tube 4 surrounds only the distal end portion of the core shaft 2. Alternatively, the outer flexible tube 4 may surround the entirety of the core shaft 2.

Figure 7:
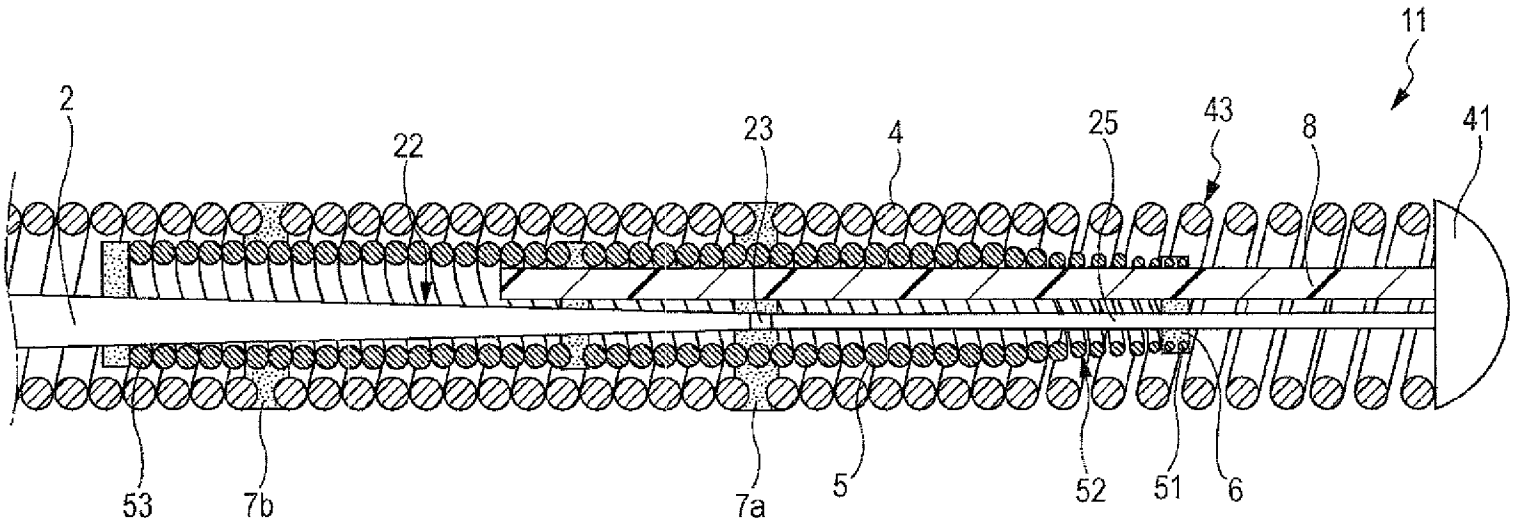
FIG. 7 is a sectional side view of a distal end portion of a guidewire according to another modification.
Figure 8:
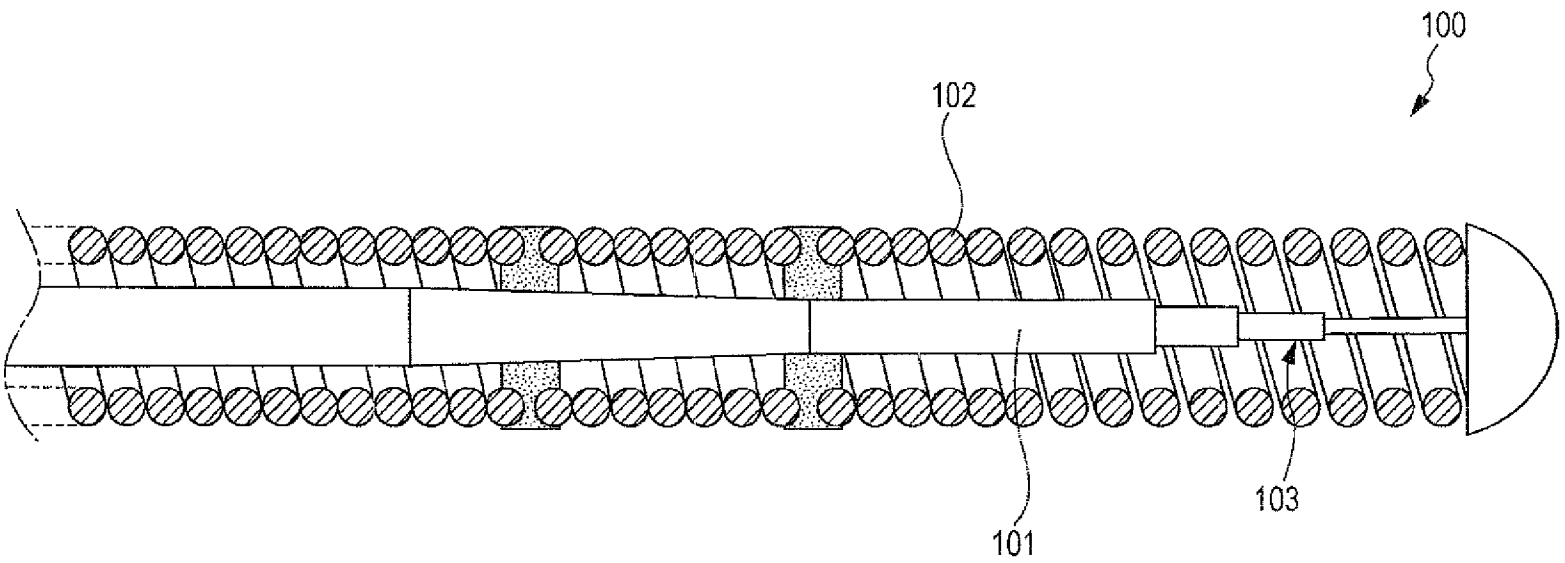
FIG. 8 is a sectional side view of a distal end portion of a guidewire of the related art.

In the first and second embodiments, only the outer flexible tube 4 and the inner flexible tube 5 are joined at the second joints 7a and 7b. Alternatively, the inside of the inner flexible tube 5 may be also fixed by soldering. That is, for example, in the guidewire 11 of the second embodiment, the second joint 7a may be formed by fixing the outer flexible tube 4, the inner flexible tube 5, the stranded wire 8, and the core shaft 2 to each other by soldering (see FIG. 7).

The present invention contains subject matter related to Japanese Patent Application No. 2009-143732 filed in the Japan Patent Office on Jun. 16, 2009, the entire contents of which are incorporated herein by reference.

What is claimed is:

1. A medical guidewire comprising:

a core shaft including a distal end portion having a small diameter;

an outer flexible tube that surrounds an outer surface of the core shaft; and an inner flexible tube disposed [in] *completely within* the outer flexible tube, the inner flexible tube surrounding the distal end portion of the core shaft, *wherein*

[wherein] a distal end of the core shaft is joined to a distal end of the outer flexible tube,

[wherein] the inner flexible tube is disposed so that a distal end thereof is positioned between the distal end of the core shaft and a proximal end of the core shaft so as to be separated from the distal end of the core shaft, [and]

[wherein] a first joint is formed so as to join the distal end of the inner flexible tube to the core shaft without jointing the outer flexible tube so as to be separated from the outer flexible tube, and at least one second joint is formed so as to join the outer flexible tube to the inner flexible tube without jointing the core shaft, the at least one second joint being positioned between the first joint and the proximal end of the inner flexible tube*, and*

*the inner flexible tube has a tapered shape in which an outside diameter of the inner flexible tube gradually decreases toward a distal end thereof.*

2. The medical guidewire according to claim 1, further comprising:

a stranded wire disposed in the inner flexible tube, the stranded wire extending from the distal end of the inner flexible tube parallel to the distal end portion of the core shaft.

[3. The medical guidewire according to claim 1, wherein an entire inner flexible tube is disposed in the outer flexible tube, and the inner flexible tube has a tapered shape in which an outside diameter gradually decreases toward a distal end thereof.]

4. The medical guidewire according to claim 1, wherein an entire inner flexible tube is disposed in the outer flexible tube, and an outside diameter of the inner flexible tube decreases stepwise toward a distal end thereof.

5. The medical guidewire according to claim 1, wherein the inner flexible tube is a hollow stranded-wire coil in which a plurality of metal strands are stranded.

6. The medical guidewire according to claim 1, wherein the outer flexible tube is a single-wire coil including a large-pitch portion extending from the distal end of the outer flexible tube toward the proximal end of the outer flexible tube by a predetermined distance, the large-pitch portion having a pitch that is larger than a pitch of a proximal end portion of the outer flexible tube, and wherein a proximal end of the large-pitch portion is positioned between the first joint and the at least one second joint.

7. A medical guidewire comprising:

a core shaft including a distal end portion having a small diameter;

an outer flexible tube that surrounds an outer surface of the core shaft; and an inner flexible tube disposed [in] *completely within* the outer flexible tube, the inner flexible tube surrounding the distal end portion of the core shaft, *wherein*

[wherein] a distal end of the core shaft is joined to a distal end of the outer flexible tube,

[wherein] the inner flexible tube is disposed so that a distal end thereof is positioned between the distal end of the core shaft and a proximal end of the core shaft so as to be separated from the distal end of the core shaft, and

[wherein] a first joint is formed so as to join the distal end of the inner flexible tube to the core shaft without jointing the outer flexible tube, at least one second joint is formed so as to join the outer flexible tube to the inner flexible tube without jointing the core shaft, and a third joint is formed so as to join the proximal end of the inner flexible tube to the core shaft without jointing the outer flexible tube, the at least one second joint being positioned between the first joint and the third joint*, and*

*the inner flexible tube has a tapered shape in which an outside diameter of the inner flexible tube gradually decreases toward a distal end thereof.*

8. The medical guidewire according to claim 7, wherein the third joint is positioned between the at least one second joint and the proximal end of the core shaft.

9. The medical guidewire according to claim 7, further comprising:

a stranded wire disposed in the inner flexible tube, the stranded wire extending from the distal end of the inner flexible tube parallel to the distal end portion of the core shaft.

[10. The medical guidewire according to claim 7, wherein an entire inner flexible tube is disposed in the outer flexible tube, and the inner flexible tube has a tapered shape in which an outside diameter gradually decreases toward a distal end thereof.]

11. The medical guidewire according to claim 7, wherein an entire inner flexible tube is disposed in the outer flexible tube, and an outside diameter of the inner flexible tube decreases stepwise toward a distal end thereof.

12. The medical guidewire according to claim 7, wherein the inner flexible tube is a hollow stranded-wire coil in which a plurality of metal strands are stranded.

13. The medical guidewire according to claim 7, wherein the outer flexible tube is a single-wire coil including a large-pitch portion extending from the distal end of the outer flexible tube toward the proximal end of the outer flexible tube by a predetermined distance, the large-pitch portion having a pitch that is larger than a pitch of a proximal end portion of the outer flexible tube, and wherein a proximal end of the large-pitch portion is positioned between the first joint and the third joint.

14. The medical guidewire according to claim 7, wherein the third joint is positioned between the at least one second joint and the proximal end of the inner flexible tube.

*15. The medical guidewire according to claim 1, wherein at least a portion of the distal end of the core shaft is made of a pseudoelastic alloy, and at least a portion of the proximal end of the core shaft is made of a stainless steel alloy.*

* * * * *